(12) United States Patent
Vandoni et al.

(10) Patent No.: US 8,168,625 B2
(45) Date of Patent: May 1, 2012

(54) PHARMACEUTICAL COMPOSITION BASED ON AGONIST OF BENZODIAZEPINE

(75) Inventors: Guido Vandoni, Correzzana (IT); Carlo Oliani, Hortolândia (BR); Adriano Coelho, Hortolândia (BR); Heny Zaniboni, Hortolândia (BR)

(73) Assignee: Sigma Pharma Ltda., Hortolandia (BR)

( * ) Notice: Subject to any disclaimer, the term of this patent is extended or adjusted under 35 U.S.C. 154(b) by 0 days.

(21) Appl. No.: 10/559,290

(22) PCT Filed: May 26, 2004

(86) PCT No.: PCT/BR2004/000076
§ 371 (c)(1),
(2), (4) Date: Dec. 2, 2005

(87) PCT Pub. No.: WO2004/105767
PCT Pub. Date: Dec. 9, 2004

(65) Prior Publication Data
US 2006/0134200 A1    Jun. 22, 2006

(30) Foreign Application Priority Data

Jun. 2, 2003 (BR) .................................... 0302017

(51) Int. Cl.
*A61K 31/55* (2006.01)
(52) U.S. Cl. ........................................................ 514/221
(58) Field of Classification Search ................... 514/221
See application file for complete search history.

(56) References Cited

U.S. PATENT DOCUMENTS 4,229,447 A * 10/1980 Porter ........................... 514/221
4,828,836 A    5/1989 Elger et al.
2004/0253307 A1 * 12/2004 Hague et al. .................. 424/464
* cited by examiner

*Primary Examiner* — Zohreh Fay
(74) *Attorney, Agent, or Firm* — Birch, Stewart, Kolasch & Birch, LLP

(57) ABSTRACT

The present invention describes the use of pharmaceutical compounds in pharmaceutical compositions for sublingual administration, including as active ingredient thereof, an agonist of the central receptor of benzodiazepinics chosen among diazepam, lorazepam, bromazepam, triazolam, alprazolam, flunitrazepam, nitrazepam and midazolam maleate, in a mixture with a pharmaceutical excipient consisting of, at least, 70% of the weight of the final formulation containing 40-45% by weight of lactose, 15-27% by weight of sorbitol and 12-16% by weight of cellulose.

4 Claims, No Drawings

PHARMACEUTICAL COMPOSITION BASED ON AGONIST OF BENZODIAZEPINE

FIELD OF APPLICATION

The present invention refers to a pharmaceutical composition for sublingual administration containing as active ingredient, an agonist of the central receptor of benzodiazepinics, chosen among diazepam, lorazepam, bromazepam, triazolam, alprazolam, flunitrazepam, nitrazepam and midazolam maleate.

STATE OF THE ART

It is well known that diazepam, lorazepam, bromazepam, triazolam, alprazolam, flunitrazepam, nitrazepam and midazolam maleate are agonists of the central receptor of benzodiazepinics used as a hypnosis inductors, as an anxyolitic in the prevention of panic attacks, in the preparation of pre-surgical manipulation, in catheterization, in small surgical interventions and, through injectable via, also as pre-anesthetics.

Due to its use as a hypnosis inductors, in the case of difficulty of dormancy, of frequent awakening or night agitation, or as an anxiolytic, in the case of needing sedation with the purpose of obtaining its myorelaxant action, the quick action of the referred to benzodiazepinics makes the quick response after its administration, essential.

Due to such characteristic, for example, the use as pre-anesthetic, some benzodiazepinics are administered through injectable via; however, some are not available in the injectable form. Therefore, it would be appreciated to have a preparation that would permit acceleration of the sedative, anxiolytical and hypnotic action of diazepam, lorazepam, bromazepam, triazolam, alprazolam, flunitrazepam, nitrazepam and midazolam maleate, without having to use the injectable via.

A sublingual pharmaceutical composition containing benzodiazepinics as diazepam, lorazepam, temazepam, oxazepam and chlordiazepoxide is described in Patent U.S. Pat. No. 4,229,447. This publication describes a sublingual tablet weighing 36 mg, containing 1 mg (2.77%) of lorazepam and containing excipients in the following ratios: 10.8 mg (30%) of microcrystalline cellulose, 3.0 mg (8.33%) of starch, 0.1 mg (0.28%) of magnesium stearate and 21.1 mg (58.61%) of lactose. The Patent describes studies on bioavailability, comparing sublingual tablets of lorazepam (2 mg) to orally soluble tablets (2 mg) and the intramuscularly injectable formulation (2 mg). The results show that the absorption of lorazepam sublingual formulation is higher during the first 60 minutes, and that the plasmatic concentration peak after the sublingual and oral administration is about 25 ng/ml and 17 ng/ml, respectively. However, the document does not describe a formulation of the composition in the oral pharmaceutical form.

SUMMARY OF THE INVENTION

It was evidenced that in case the central agonists of benzodiazepinics chosen among the group composed of diazepam, lorazepam, bromazepam, triazolam, alprazolam, flunitrazepam, nitrazepam and midazolam maleate, administered by sublingual via in pharmaceutical compositions with essential carrier containing, at least, 70% of the diluents constituted by ternary mixture of the essential excipients lactose/sorbitol/celullose in specific percentages, show an extremely quick absorption of the medicament resulting in quick action of the referred to medicament, similar to that of the injectable preparations, and greater than in the formulations of the sublingual tablets containing lorazepam, described in Patent U.S. Pat. No. 4,229,447.

The term in English "essential carrier" in the present invention refers to the pharmaceutical composition containing a mixture of the active ingredient composed of central agonists of benzodiazepinics chosen among the group composed of diazepam, lorazepam, bromazepam, triazolam, alprazolam, flunitrazepam, nitrazepam and midazolam maleate and the excipients necessary to compose the formulation shown in the form of sublingual tablet for oral administration, especially including the essential excipients. The term in English "essential excipients", in the present patent application refers to the mixture of the excipients or the ternary mixture lactose/cellulose/sorbitol in specific proportions lactose (40-45% by weight)/cellulose (12-16% by weight)/sorbitol (5-27% by weight) in a proportion of 3/1.4-2.7/1. The term in English "ternary mixture", in the present patent application, refers to the mixture of the three excipients lactose/cellulose/sorbitol. Hereinafter, the terms essential carrier, essential excipients and ternary mixture will appear in the present document designating the one previously explained.

DETAILED DESCRIPTION OF THE INVENTION

Therefore, this invention provides a pharmaceutical composition for sublingual administration containing, as one active ingredient, an agonist of the central receptor of the group of benzodiazepinics chosen among diazepam, lorazepam, bromazepam, triazolam, alprazolam, flunitrazepam, nitrazepam and midazolam maleate in a mixture with an essential excipient composed of, at least, 70% of the weight of the final formulation preferably containing 75-85% of the ternary mixture, as for example 40-45% by weight of lactose, 15-27% by weight of sorbitol and 12-16% by weight of cellulose.

Such pharmaceutical composition composed of tablets for sublingual administration is directed to the quick induction of sedation, anxiolysis and sleep in patients needing such induction.

A ternary mixture composed of essential excipients lactose/cellulose/sorbitol used in specific percentages, constitute a composition containing lactose/cellulose/sorbitol in the following percentage composition: 3.0, 1.4-2.7 and 1. It is know that the essential excipients may be added to formulations, together with other excipients as diluents, lubricants, aggregating, edulcorants, taste correctors (flavors) and, eventually, disaggregating agents used in the manufacture of orally soluble tablets and tablets for sublingual use in advantageous form.

The preferable dosage unit of the referred to agonists are of 2, 5 or 10 mg of diazepam, 1 or 2.5 mg of lorazepam, 1.5, 3 or 6 mg of bromazepam, 0.125 or 0.25 mg of triazolam, 0.25, 0.50 or 1 mg of alprazolam, 1 or 2 mg of flunitrazepam, 5 mg of nitrazepam and 5 or 15 mg of midazolam maleate. In the sublingual pharmaceutical composition, the agonist is preferably present in quantities of 0.125-10% relative to weight of final composition.

The lubricants, magnesium sterate and/or polyethylene glycol 6000 are used in quantities corresponding to 0.5-5% by weight. The aggregating agents, as metylcellulose and sodium carboxymetylcellulose are advantageously used in variable percentages, by weight, from 0 to 10%. The disaggregating agents, as crospovidone or polyvinyl pirrolidone do not exceed 6%.

Due to the sublingual use of the pharmaceutical preparation of the present invention, the edulcorants and/or the flavors constitute an essential presence and will be chosen according to the affinity of the same with the organoleptic characteristics of any active ingredient. Therefore, the synthetic edulcorants, as sodium saccharine or aspartame, are being used in quantities of 0.1-2%. The flavors incorporated in the composition may also be chosen between the flavors and fragrances of synthetic or natural oils, among the latter are the extracts of plants, leaves, flowers, fruits and combinations thereof, such as the oil of cinnamon, mint like "menta piperita", anise, cedar leaves, sour almonds, citric fruits, specially orange and lemon, chamomile and grapefruit. The flavor of vanilla or eucalyptus and the essences of fruits, specially apple, pear, peach, raspberry, cherry, apricot and grape may also be advantageously used. Generally, the flavors are present in quantities that vary from 0.05% to 4%, relative to the total weight of the composition. The preferred flavors are those resulting in mint or fruit flavor, particularly of grape, cherry or citric fruits, especially orange, lemon or tropical fruits or also the mixture thereof.

According to other aspects, the present invention provides pharmaceutical compositions in the form of sublingual tablets and shows the following percentage composition: 0.125-10% of the active ingredient chosen among the group formed by diazepam, lorazepam, bromazepam, triazolam, alprazolam, flunitrazepam, nitrazepam midazolam maleate; being the essential excipients 75-85% of the total weight of the pharmaceutical composition, preferably in the proportion of 3/1.4-2.7/1; 0.5-5% of a lubricant; 0-10% of an aggregating agent chosen among the soluble derivatives of cellulose as the carboxymetylcellulose; 0.4-0.6% of synthetic edulcorant and 1-2.5% of one or more flavors.

Therefore, the sublingual tablets of the present invention show weight of 80-250 mg and contain the above mentioned quantity of diazepam (2.5 to 10 mg), lorazepam (1 to 2.5 mg), bromazepam (1.5 to 6 mg), triazolam (0.125 to 0.25 mg), alprazolam (0.25 to 1 mg), flunitrazepam (1 to 2 mg), nitrazepam (5 mg) and midazolam stearate (5 to 15 mg) as one active ingredients. Preferably, the sublingual tablets have in its composition, 75-85% of the weight of the total composition constituted of essential excipients in the proportion of 3/1.4-2.7/1; 0.5% of magnesium stearate as lubricant; sodium carboxymetylcellulose as aggregating agent; crospovidone as disaggregating agent, sodium saccharine as artificial edulcorant and, at least, one flavoring, all in the above mentioned percentage quantities.

The tablets are preferably formed by 0.125 to 10% of the active ingredient in the above mentioned dosages, by 75-85% of the weight of the total composition constituted by the ternary mixture of the essential excipients in the proportion of 3/1.4-2.7/1, being the remaining part constituted by a mixture of diluents: 6-15% of corn starch; by 0.5-1% of magnesium stearate as lubricant; by 0.1 to 1% of sodium saccharin as edulcorant; by 0.05 to 2.5% of lemon or orange flavor or combinations thereof, 0-5% of crospovidone as disintegrating agent; 0-0.005% of coloring of beta-carotene, carmine, yellow or red iron oxide. Preferably, the sublingual tablets of the present invention weigh from 80 to 200 mg and contain the above mentioned quantity of diazepam, lorazepam, bromazepam, triazolam, alprazolam, flunitrazepam, nitrazepam and midazolam maleate, in the quantity of essential excipients and other excipients as previously shown.

The tablets for sublingual administration of the present invention may be manufactured according to the classic methods used in the pharmaceutical technique, for example, through direct compression, by wet granulation or using technologies which, through the addition of the active ingredient in the form of micro-granules, micro-spheres or micro-emulsions, allow a better absorption of the referred to active ingredient.

The bioavailability after the sublingual administration of the single dose of pharmaceutical composition representing three agonists, diazepam 10 mg, lorazepam 2.5 mg and bromazepam 6 mg, according to the formulation described hereunder in Examples I-III, was compared in studies with the single dose pharmaceutical composition of conventional oral tablets (orally soluble) of the three active ingredients in the same dosages. Three studies were carried out, each of them with eight healthy volunteers of the male sex, recruited after information on the nature and characteristics of the principles included in the scope of the study. Each study, composed of two periods of treatment, was carried out according to a crossed and randomized scheme. All individuals received the previously established dose of the active ingredient in the form of conventional oral tablets and sublingual tablets, with a period of detoxication of, at least, seven days between the first and the following administration, according to a previously established randomized list. The sublingual tablets were placed under the tongue until complete dissolution, in correspondence with the venous plexus, while the conventional oral tablets were swallowed unbroken with 150 ml of mineral water. Within the intervals of 0-20-40 minutes, 1-1,5-2-2,5-3-3,5-4-6-8-10-1 l 2 and 24 hours after the treatment, 5 ml of blood were collected. The relevant average plasmatic rates (ng/ml) after the referred to single doses are presented in Table I.

TABLE I

| Time Schedule | DIAZEPAM | | LORAZEPAM | | BROMAZEPAN | |
|---|---|---|---|---|---|---|
| | Sublingual | Oral | Sublingual | Oral | Sublingual | Oral |
| 0 min | 0 | 0 | 0 | 0 | 0 | o |
| 20 min | 193.9 ± 31.9 | 51.9 ± 7.6 | 44.5 ± 5.9 | 30.8 ± 9.4 | 80.8 ± 11.3 | 69.0 ± 10.1 |
| 40 min | 308.5 ± 36.9 | 106.0 ± 13.3 | 56.5 ± 8.5 | 41.0 ± 10.44 | 108.8 ± 22.1 | 91.7 ± 5.6 |
| 1 H | 274.0 ± 31.4 | 275.9 ± 45.6 | 47.9 ± 8.5 | 46.1 ± 7.9 | 109.6 ± 15.2 | 116.8 ± 14.9 |
| 1.5 H | 210.4 ± 21.4 | 279.8 ± 36.0 | 41.4 ± 8.8 | 47.8 ± 8.5 | 94.4 ± 10.4 | 108.1 ± 15.3 |
| 2 H | 177.9 ± 13.5 | 235.0 ± 26.1 | 37.2 ± 7.7 | 47.3 ± 9.1 | 84.0 ± 5.7 | 91.6 ± 9.7 |
| 2.5 H | 162.5 ± 14.7 | 203.1 ± 21.7 | 32.2 ± 4.4 | 39.0 ± 10.2 | 74.2 ± 5.7 | 77.2 ± 5.9 |
| 3 H | 156.6 ± 12.1 | 183.1 ± 19.4 | 28.3 ± 4.2 | 33.4 ± 10.3 | 67.9 ± 6.1 | 70.2 ± 6.8 |
| 3.5 H | 145.8 ± 10.6 | 165.9 ± 17.9 | n.d.* | n.d.* | n.d.* | n.d.* |
| 4 H | 132.2 ± 11.7 | 154.6 ± 17.0 | 25.6 ± 5.0 | 28.2 ± 8.4 | 63.4 ± 5.5 | 63.1 ± 6.9 |
| 6 H | 122.7 ± 9.0 | 133.8 ± 14.4 | 22.8 ± 4.61 | 22.6 ± 5.7 | 57.1 ± 5.0 | 53.4 ± 4.8 |

TABLE I-continued

| Time Schedule | DIAZEPAM Sublingual | DIAZEPAM Oral | LORAZEPAM Sublingual | LORAZEPAM Oral | BROMAZEPAN Sublingual | BROMAZEPAN Oral |
|---|---|---|---|---|---|---|
| 8 H | 111.1 ± 5.54 | 119.3 ± 13.1 | 9.6 ± 3.7 | 19.6 ± 4.8 | 49.4 ± 7.0 | 49.1 ± 4.4 |
| 10 H | 102.8 ± 5.3 | 109.5 ± 13.8 | 17.6 ± 2.6 | 16.6 ± 3.5 | 44.8 ± 6.2 | 42.7 ± 3.1 |
| 12 H | 94.8 ± 8.9 | 103.4 ± 15.2 | 14.5 ± 2.3 | 13.5 ± 2.3 | 38.8 ± 5.6 | 37.9 ± 3.0 |
| 24 H | 83.3 ± 11.1 | 94.4 ± 14.0 | 10.3 ± 1.1 | 10.6 ± 1.7 | 33.5 ± 6.1 | 30.2 ± 3.8 | n.d. = non-determined

As can be noted in this table, the plasmatic rates of the three products may be superposed, except for diazepam in the first hour, which after the sublingual administration shows hematological rates definitely higher in relation to those obtained in the first hour after the oral administration.

The several pharmacokinetic parameters (average±standard deviation) referring to the sublingual administration of the three benzodiazepinics mentioned above, especially for $AUC_{0-t}$, i.e., the area under the curve as from time 0 up to time T (in this case, in hour 24), its logarithm, $AUC_{0-inf}$ (in ng/ml/h), represents the area under the curve calculated according to the formula $$AUC_{0-inf} = AUC_{0-t} + C_t/\beta$$

where $C_t$ is the plasmatic concentration (in ng/ml) estimated for time T (in this case 24 hours) and $\beta$ is the slope of the curve of the elimination phase, being its logarithm, the $C_{max}$ (in ng/ml), i.e., the peak of maximum concentration, being its logarithm and the $T_{max}$, i.e., the time (in hours) in which the maximum plasmatic concentration peak was compared, all according to the information in Table II.

TABLE II

| * | DIAZEPAM Sublingual | DIAZEPAM Oral | LORAZEPAM Sublingual | LORAZEPAM Oral | BROMAZEPAM Sublingual | BROMAZEPAM Oral |
|---|---|---|---|---|---|---|
| A | 2733.28 ± 143.99 | 2906.95 ± 287.27 | 451.96 ± 53.01 | 453.68 ± 74.13 | 1156.11 ± 102.10 | 1125.03 ± 60.22 |
| B | 4967.69 ± 743.32 | 5390.68 ± 1130.93 | 621.03 ± 70.06 | 655.62 ± 142.92 | 1903.00 ± 325.99 | 1761.83 ± 223.39 |
| l-A | 3.44 ± 0.02 | 3.46 ± 0.04 | 6.11 ± 0.13 | 2.65 ± 0.08 | 3.06 ± 0.04 | 3.05 ± 0.02 |
| l-B | 3.69 ± 0.07 | 3.72 ± 0.09 | 6.43 ± 0.12 | 2.81 ± 0.10 | 3.27 ± 0.09 | 3.24 ± 0.06 |
| C | 321.75 ± 13.35 | 307.64 ± 30.17 | 56.88 ± 8.41 | 54.44 ± 4.98 | 120.50 ± 12.06 | 124.73 ± 9.81 |
| l-C | 2.51 ± 0.02 | 2.49 ± 0.04 | 4.03 ± 0.16 | 1.73 ± 0.04 | 2.08 ± 0.04 | 2.10 ± 0.03 |
| $T_{max}$ | 0.75 ± 0.15 | 1.25 ± 0.27 | 0.71 ± 012 | 1.52 ± 0.49 | 0.75 ± 0.15 | 1.25 ± 0.38 |

*A = $AUC_{0-t}$, B = $AUC_{0-inf}$; l-A = log $AUC_{0-t}$, l-B = log $AUC_{0-inf}$; C = $C_{max}$, l-C = log $C_{max}$.

The data in Table II refers to the pharmacokinetic data $AUC_{0-t}$, $AUC_{0-inf}$ and its logarithms, $C_{max}$ and log $C_{max}$ are not statistically significant, while the results for $T_{max}$ are statistically significant (P<0,01).

The already mentioned Table II indicates that AUC and $C_{max}$ for diazepam, lorazepam and bromazepam are comparable, while the $T_{max}$ after sublingual administration show a reduction of approximately 30 minutes, thus showing that these products, when administered by sublingual via show higher action speed in relation to that obtained after the administration of the conventional oral preparations.

One of the studies illustrated above was conducted in the three via of administration, inclusive comparing the sublingual formulation of Example II, described in Table III as "New Formulation" containing 2.5 mg of lorazepam, and the existing "Known Formulation" of lorazepam 2.5 mg containing the same "essential excipients" and in the same proportion indicated in Patent U.S. Pat. No. 4,229,442. Table III shows the results obtained using the same procedures and the same number of volunteers (eight) according to the same methods previously described.

TABLE III

Blood levels of Lorazepam (ng/ml)

| Timetable | New formulation | Known Formulation |
|---|---|---|
| 0 | 0 | 0 |
| 20 min | 44.5 ± 5.9 | 35.5 ± 7.5 |
| 40 min | 56.5 ± 8.5 | 43.1 ± 8.0 |
| 1 hr | 47.9 ± 8.5 | 41.0 ± 6.3 |
| 1.5 hr | 41.5 ± 8.8 | 33.8 ± 6.8 |
| 2 hr | 37.2 ± 7.7 | 28.6 ± 6.7 |
| 2.5 hr | 32.2 ± 4.4 | 28.4 ± 5.8 |
| 3 hr | 28.3 ± 4.2 | 25.0 ± 5.9 |
| 4 hr | 25.6 ± 5.0 | 22.7 ± 5.7 |
| 6 hr | 22.8 ± 4.6 | 20.1 ± 5.2 |
| 8 hr | 19.6 ± 3.7 | 17.3 ± 5.0 |
| 10 hr | 17.6 ± 2.6 | 12.8 ± 2.5 |
| 12 hr | 14.5 ± 2.3 | 10.2 ± 2.6 |
| 24 hr | 10.3 ± 1.1 | 8.2 ± 3.6 |

TABLE IV

Lorazepam

| | New formulation | Known formulation |
|---|---|---|
| A | 451.96 ± 53.01 | 362.62 ± 62.61 |
| B | 621.03 ± 70.06 | 514.36 ± 95.92 |
| 1A | 6.11 ± 0.13 | 5.88 ± 0.17 |
| 1B | 6.43 ± 0.12 | 6.23 ± 0.20 |
| C | 56.88 ± 8.41 | 44.04 ± 7.35 |
| 1C | 4.03 ± 0.16 | 3.77 ± 0.16 |
| $T_{max}$ | 0.71 ± 0.12 | 0.75 ± 0.16 |

A=AUC 0-t; B=AUC 0-inf; 1A=log AUC 0-t; 1B=log AUC 0-inf; C=$C_{max}$; 1C=log Cmax.

The data from Table IV referring to the AUC pharmacokinetic data and its logarithms, $C_{max}$ and log $C_{max}$, show a significant difference (p<0,01) between the two formulations as shown in $AUC_{0-t}$ and $C_{max}$ data, indicating better bioavailability in the formulation described in Example II hereunder. The following examples illustrate the invention, without limiting the same in any form.

EXAMPLE I

Sublingual Tablets Containing 10 mg of Diazepam

One kilogram of diazepam and 1.2 kg of corn starch are mixed during 15 minutes until complete homogenization (mixture 1). The same goes through a 35 mesh. The following is added to the mixture: 0.2 kg of orange flavor powder, 0.05 kg of sodium saccharine, 4.38 kg of lactose, 1.47 kg of cellulose microcrystalline and 1.65 kg sorbitol micro-granules, making these components go through a sieve of 35 mesh corresponding to approximately 500 micros. Such mixture is homogenized for about 15 minutes in a mixer of V type, finally adding 0.05 kg of magnesium stearate, continuing to mix during 5 minutes. The final mixture is submitted to compression in a tablet-manufacturing machine, provided with punches with 6 mm diameter, which should have both flat surfaces, or both hollow surfaces or also the upper surface hollow and lower surface plain. Thus, 100.000 sublingual tablets will be obtained, all equal and with a weight of 100 mg, with the following composition:

| | |
|---|---|
| Diazepam | 10.00 mg |
| Corn starch | 12.00 mg |
| Magnesium stearate | 0.5 mg |
| Orange flavor powder | 2.00 mg |
| Sodium Saccharine | 0.50 mg |
| Lactose | 43.80 mg |
| Cellulose powder | 14.70 mg |
| Sorbitol micro-granulated | 16.50 mg |

EXAMPLE II

Sublingual Tablets Containing 2.5 mg of Lorazepam

Working as described in Example I, the sublingual tablets are prepared with individual weight of 100 mg, according to the following composition:

| | |
|---|---|
| Lorazepam | 2.50 mg |
| Corn starch | 12.00 mg |
| Magnesium stearate | 0.50 mg |
| Orange flavor powder | 2.00 mg |
| Sodium saccharine | 0.50 mg |
| Lactose | 43.80 mg |
| Cellulose microcrystalline | 14.70 mg |
| Sorbitol micro-granulated | 24.00 mg |

EXAMPLE III

Sublingual Tablets Containing 6 mg of Bromazepam

Working as described in Example I, the sublingual tablets are prepared with individual weight of 100 mg, according to the following composition:

| | |
|---|---|
| Bromazepam | 6.00 mg |
| Corn starch | 12.00 mg |
| Magnesium stearate | 0.50 mg |
| Orange flavor powder | 2.00 mg |
| Sodium saccharine | 0.50 mg |
| Lactose | 43.80 mg |
| Cellulose powder | 14.70 mg |
| Sorbitol micro-granulated | 20.50 mg |

EXAMPLE IV

Sublingual Tablets Containing 10 mg of Diazepam

Working as described in Example I, the sublingual tablets are prepared with individual weight of 100 mg, containing 10 mg of diazepam, being 75% of the weight of essential excipients lactose/cellulose/sorbitol in a proportion of 2.97/2.65/1, corresponding to the percentages of 43.80/16.50/14.70%. The tablets have the following composition:

| | |
|---|---|
| Diazepam | 10.00 mg |
| Corn starch | 8.00 mg |
| Orange flavor powder | 2.00 mg |
| Sodium saccharine | 0.50 mg |
| Lactose | 43.80 mg |
| Sorbitol micro-granulated | 16.50 mg |
| Cellulose powder | 14.70 mg |
| Magnesium stearate | 0.50 mg |
| Crospovidone | 4.00 mg |

EXAMPLE V

Sublingual Tablets Containing 5 mg of Diazepam

Working as described in Example I, the sublingual tablets are prepared with individual weight of 100 mg, containing 5 mg of diazepam, being 80% of the weight of essential excipients lactose/cellulose/sorbitol in a proportion of 2.97/2.03/1, corresponding to the percentages of 43.80/21.50/14.70%. The tablets have the following composition:

| | |
|---|---|
| Diazepam | 5.00 mg |
| Iron oxide, yellow USP | 0.04 mg |
| Corn starch | 8.00 mg |
| Orange flavor powder | 2.00 mg |
| Sodium saccharine | 0.50 mg |
| Lactose | 43.80 mg |
| Sorbitol micro-granulated | 21.50 mg |
| Cellulose powder | 14.70 mg |
| Magnesium stearate | 0.50 mg |
| Crospovidone | 4.00 mg |

EXAMPLE VI

Sublingual Tablets Containing 1,5 mg of Bromazepam

Working as described in Example I, the sublingual tablets are prepared with individual weight of 100 mg, containing 1.5 mg of bromazepam, being 83.5% of the weight of essential excipients lactose/cellulose/sorbitol in a proportion of 2.97/1.75/1, corresponding to the percentages of 43.8/25/14.70%. The tablets have the following composition:

| | | |
|---|---|---|
| Bromazepam | 1.50 | mg |
| Iron oxide, red USP | 0.02 | mg |
| Corn starch | 8.00 | mg |
| Orange flavor powder | 2.00 | mg |
| Sodium saccharine | 0.50 | mg |
| Lactose | 43.80 | mg |
| Sorbitol micro-granulated | 25.00 | mg |
| Cellulose powder | 14.70 | mg |
| Magnesium stearate | 0.50 | mg |
| Crospovidone | 4.00 | mg |

EXAMPLE VII

Sublingual Tablets Containing 3 mg of Bromazepam

Working as described in Example I, the sublingual tablets are prepared with individual weight of 100 mg, containing 3 mg of bromazepam, being 82% of the weight of essential excipients lactose/cellulose/sorbitol in a proportion of 2.97/1.86/1, corresponding to the percentages of 43.8/23.5/14.70%. The tablets have the following composition:

| | | |
|---|---|---|
| Bromazepam | 3.00 | mg |
| Iron oxide, yellow USP | 0.04 | mg |
| Corn starch | 8.00 | mg |
| Orange flavor powder | 2.00 | mg |
| Sodium saccharine | 0.50 | mg |
| Lactose | 43.80 | mg |
| Sorbitol micro-granulated | 23.50 | mg |
| Cellulose powder | 14.70 | mg |
| Magnesium stearate | 0.50 | mg |
| Crospovidone | 4.00 | mg |

EXAMPLE VIII

Sublingual Tablets Containing 6 mg of Bromazepam

Working as described in Example I, the sublingual tablets are prepared with individual weight of 100 mg, containing 6 mg of bromazepam, being 79% of the weight of essential excipients lactose/cellulose/sorbitol in a proportion of 2.97/2.14/1, corresponding to the percentages of 43.80/20.5/4.70%. The tablets have the following composition:

| | | |
|---|---|---|
| Bromazepam | 6.00 | mg |
| Corn starch | 8.00 | mg |
| Orange flavor powder | 2.00 | mg |
| Sodium saccharine | 0.50 | mg |
| Lactose | 43.80 | mg |
| Sorbitol micro-granulated | 20.50 | mg |
| Cellulose powder | 14.70 | mg |
| Magnesium stearate | 0.50 | mg |
| Crospovidone | 4.00 | mg |

The invention claimed is:

1. A pharmaceutical composition formulated for sublingual administration comprising:
    (a) about 2.5% lorazepam and
    (b) at least 76% by weight of the composition of excipients, wherein said excipients comprise by weight proportion of the final composition about 44% of lactose, about 24% of sorbitol and about 15% of cellulose,
    wherein said composition when administered sublingually obtains a maximal plasma concentration of lorazepam within 45 minutes of administration.

2. The pharmaceutical composition according to claim 1, wherein said excipients comprise 76% to 85% of the final weight of the pharmaceutical composition.

3. The pharmaceutical composition according to claim 1, further comprising at least one member of the group consisting of diluents, lubricants, aggregating, edulcorants, taste correctors, flavors and disaggregating agents.

4. The pharmaceutical composition according to claim 1, wherein said excipients comprise 76% to 85% of the final weight of the pharmaceutical composition, and wherein said composition further comprises a mixture of 6-15% of corn starch, 0.5-1% of magnesium stearate as lubricant; by 0.1 to 1% of sodium saccharine; 0.05 to 2.5% of lemon, orange flavor or its combinations; by 0 to 5% of crospovidone as disintegrating agent, and 0 to 0.05% of coloring.

\* \* \* \* \*